United States Patent
Takeda et al.

(10) Patent No.: US 9,845,278 B2
(45) Date of Patent: Dec. 19, 2017

(54) METHOD FOR IMPROVING PRESERVATION STABILITY OF 2,2-DIFLUOROACETALDEHYDE

(71) Applicant: Central Glass Company, Limited, Ube-shi, Yamaguchi (JP)

(72) Inventors: Masaaki Takeda, Kawagoe (JP); Shinya Akiba, Kawagoe (JP); Ryo Nadano, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 15/326,808

(22) PCT Filed: Jun. 19, 2015

(86) PCT No.: PCT/JP2015/067750
§ 371 (c)(1),
(2) Date: Jan. 17, 2017

(87) PCT Pub. No.: WO2016/017318
PCT Pub. Date: Feb. 4, 2016

(65) Prior Publication Data
US 2017/0197899 A1  Jul. 13, 2017

(30) Foreign Application Priority Data

Jul. 30, 2014  (JP) ................ 2014-155544

(51) Int. Cl.
C07C 45/86  (2006.01)
C07C 41/00  (2006.01)
C07C 41/50  (2006.01)

(52) U.S. Cl.
CPC .............. *C07C 45/86* (2013.01); *C07C 41/50* (2013.01)

(58) Field of Classification Search
CPC .................. C07C 45/86; C07C 41/50
See application file for complete search history.

(56) References Cited

U.S. PATENT DOCUMENTS

| | | |
|---|---|---|
| 5,248,832 A | 9/1993 | Lee |
| 2007/0275980 A1 | 11/2007 | Yoshida et al. |
| 2009/0247786 A1 | 10/2009 | Komata et al. |
| 2010/0190863 A1 | 7/2010 | Martin et al. |
| 2015/0329455 A1 | 11/2015 | Ootsuka et al. |

FOREIGN PATENT DOCUMENTS

| | | |
|---|---|---|
| EP | 0 516 311 A1 | 12/1992 |
| EP | 2 949 639 A1 | 12/2015 |
| JP | 50-12405 | 5/1975 |
| JP | 5-170693 A | 7/1993 |
| JP | 6-263684 A | 9/1994 |
| JP | 10-338655 A | 12/1998 |
| JP | 2006-104085 A | 4/2006 |
| JP | 2007-145766 A | 6/2007 |
| JP | 2010-523600 A | 7/2010 |
| JP | 2010-209073 A | 9/2010 |
| WO | WO 2014/115801 A1 | 7/2014 |

OTHER PUBLICATIONS

D. R. Husted et al., "The Chemistry of the Perfluoro Acids and Their Derivatives. III. The Perfluoro Aldehydes," J. Am. Chem. Soc., Jan. 1, 1952, pp. 5422-5426, vol. 74, XP055384532.
Extended European Search Report issued in counterpart European Application No. 15827733.5 dated Jul. 10, 2017 (six (6) pages).
International Search Report (PCT/ISA/210) issued in PCT Application No. PCT/JP2015/067750 dated Sep. 8, 2015 with English translation (5 pages).
Japanese-language Written Opinion (PCT/ISA/237) issued in PCT Application No. PCT/JP2015/067750 dated Sep. 8, 2015 (3 pages).
Kaneko et al., "A Remarkably Simple Route to Versatile Difluoromethylated Molecules", J. Org. Chem, 1993, vol. 58, pp. 2302-2312.
Saegusa, "Polymerization of Alehyde", Synthetic Organic Chemistry, 1961, vol. 19, No. 3, pp. 254-260, with English-language abstract.
Daignault et al., "2-Cyclohexyloxyethanol", Organic Syntheses, Coll., 1973, vol. 5, p. 303 (4 pages total).
Salaun et al., "Cyclopropane Ethyl Hemiacetal from Ethyl 3-Chloropranoate", Organic Syntheses, Coll, 1990, vol. 7, p. 131(6 pages total).
Greene et a., "Protective Groups in Organic Synthesis, Third Edition", John Wiley & Sons, Inc., 1999 (28 pages total).

*Primary Examiner* — Sikarl Witherspoon
(74) *Attorney, Agent, or Firm* — Crowell & Moring LLP

(57) ABSTRACT

A method for improving preservation stability of 2,2-difluoroacetaldehyde according to the present invention include at least: a first step of forming a "2,2-difluoroacetaldehyde-alcohol composite system" in which a 2,2-difluoroacetaldehyde hemiacetal coexists with an excess alcohol, wherein the total molar amount of the alcohol is 1.15 to 4.00 times the total molar amount of 2,2-difluoroacetaldehyde; and a second step of storing, in a storage container, the "2,2-difluoroacetaldehyde-alcohol composite system" formed in the first step. It is possible by this method to suppress the conversion of the 2,2-difluoroacetaldehyde hemiacetal to a dimer and maintain the original aldehyde activity of the target compound with less composition change over a long term.

18 Claims, No Drawings

METHOD FOR IMPROVING PRESERVATION STABILITY OF 2,2-DIFLUOROACETALDEHYDE

FIELD OF THE INVENTION

The present invention relates to a method for improving the preservation stability of 2,2-difluoroacetaldehyde (hereinafter also referred to as "DFAL").

BACKGROUND ART

It is known that 2,2-difluoroacetaldehyde, which is represented by the formula (1), is a compound useful as a raw material for production of advanced materials or an intermediate for production of pharmaceutical and agrichemical products.

$$CHF_2-CHO \qquad (1)$$

In particular, 2,2-difluoroacetaldehyde has a difluoromethyl group ($-CHF_2$) in which two fluorine atoms of high electronegativity and one hydrogen atom are bonded to the same carbon atom. It is considered that this specific structure is deeply relevant to the properties of various materials produced therewith, such as water repellency, transparency, low dielectric constant, peculiar physiological activity and mimic effect. Consequently, materials produced using 2,2-difluoroacetaldehyde as building blocks are becoming subjects of vigorous researches and developments in the fields of advanced materials and pharmaceutical and agrichemical intermediates.

For example, Patent Document 1 proposes the use of 2,2-difluoroacetaldehyde as a raw material for production of hydroxyl carbonyl halides useful as pharmaceutical and agrichemical intermediates. Patent Document 2 proposes the use of 2,2-difluoroacetaldehyde as a raw material for production of novel insecticides.

There is conventionally known a method of synthesizing 2,2-difluoroacetaldehyde by partial reduction of an α,α-difluoroacetate with a hydride reduction agent such as lithium aluminum hydride (see Non-Patent Document 1). By contrast, the present applicant has filed a patent application based on the findings that it is possible to synthesize 2,2-difluoroacetaldehyde by contact of an α,α-difluoroacetate with hydrogen ($H_2$) gas in the presence of a specific ruthenium complex as a catalyst (see Patent Document 3).

On the other hand, it is known that an aldehyde is unstable and loses its aldehyde activity due to gradual polymerization of aldehyde molecules (see Non-Patent Document 2). Thus, proposed is a method of preventing polymerization of an aldehyde by providing the aldehyde in aqueous solution (hydrate) form and mixing therewith a specific surfactant, a pH modifier and a buffer (see Patent Document 4). Also proposed is a method of converting an aldehyde to a stable acetal by contact with a large excessive amount of alcohol (see Non-Patent Document 3).

PRIOR ART DOCUMENTS

Patent Documents

Patent Document 1: Japanese Laid-Open Patent Publication No. H06-263684
Patent Document 2: Japanese Laid-Open Patent Publication No. 2010-209073
Patent Document 3: International Publication No. 2014/115801
Patent Document 4: Japanese Laid-Open Patent Publication No. 2010-523600

Non-Patent Documents

Non-Patent Document 1: J. Org. Chem., vol. 58 (1993), p. 2302-2312
Non-Patent Document 2: Synthetic Organic Chemistry, vol. 19, no. 3 (1961), p. 254-260
Non-Patent Document 3: Org. Synth., vol. 7 (1990), p. 131

SUMMARY OF THE INVENTION

Problems to be Solved by the Invention

The method in which the aldehyde is provided in aqueous solution (hydrate) form as proposed by Patent Document 4 is an effective technique for stable preservation of the aldehyde. In this method, however, it is necessary to let a plurality of substances such as surfactant coexist in the system. Further, there is a problem that it is difficult to prevent polymerization of the aldehyde unless the pH of the solution system is strictly controlled. It is also necessary to perform strong dehydration on the system immediately before use of the aldehyde as a reagent (see, for example, Japanese Patent No. S50-12405). From the comprehensive viewpoint, this method tends to be complicated in operation.

The method in which the aldehyde is converted to the acetal (that is a chemical species having two alcohol molecules bound to one aldehyde molecule) by contact with the alcohol is also a superior technique for stabilization of the aldehyde.

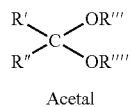

Acetal

In this method, however, it is necessary to let the aldehyde coexist with the large excessive amount of alcohol. Unless the large excessive amount of alcohol is present in the system, the aldehyde is not always converted to the acetal. It is also necessary to perform strong dehydration on the system for preservation of the acetal. Further, the acetal is readily converted to a hydrate or hemiacetal by moisture absorption during storage so that the composition of the solution system changes due to such conversion reaction. In addition, the acetal itself is a stable chemical species. Since the center carbon atom of the acetal is low in activity, it is less likely that the acetal as it is would show the original aldehyde activity as compared to the corresponding aldehyde or hemiacetal (that is a chemical species having only one alcohol molecule bound to one aldehyde molecule). It is thus often necessary to perform any treatment for converting the acetal back to the "chemically active species (such as free aldehyde)" before use as a reagent. This makes the method complicated in operation.

As an alternative to the above-mentioned methods, a novel method has been demanded for stable preservation of 2,2-difluoroacetaldehyde, that is, the target compound of the present invention.

Under these circumstances, the present inventors have made various researches about the method of stabilizing 2,2-difluoroacetaldehyde in the form of a hemiacetal, in which one alcohol molecule is bound to one aldehyde molecule, without being converted to an acetal. As a result of those researches, the present inventors have found that: a hemiacetal of the formula (3) in which one alcohol molecule of the formula (3) is bound to 2,2-difluoroacetaldehyde molecule has considerably high stability; and, by converting 2,2-difluoroacetaldehyde to the hemiacetal, it is possible to adequately suppress the occurrence of "polymerization" described in Non-Patent Document 2 (that is a phenomenon in which the molecular weight increases with successive formation of C—C bonds).

  (2)

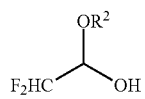  (3)

In the above formulas, $R^2$ represents a $C_1$-$C_6$ linear, branched or cyclic hydrocarbon group in which a part or all of hydrogen atoms may be substituted with a fluorine atom.

The present inventors have however also found another problem that, during storage of the hemiacetal of the formula (3) for a long term (e.g. several months or longer), the composition of the solution system changes with gradual formation of a compound of the following formula (4) (hereinafter also referred to as "dimer").

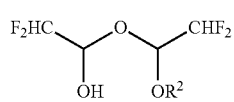  (4)

In many cases, $R^2$ of the dimer corresponds to $R^2$ of the alcohol present in the greatest amount in the system. In the case where the alcohol is mainly ethanol as in the after-mentioned examples, $R^2$ of the dimer is ethyl. The dimer is totally different from the aldehyde polymer described in Non-Patent Document 2 (in which C—C bonds continue) and is one kind of stable equivalent (i.e. hemiacetal) of 2,2-difluoroacetaldehyde that can be converted back to the original aldehyde by e.g. strong heating with the addition of an acid.

However, this dimer is a chemical species much more stable than the hemiacetal of the formula (3). It is thus not easy to cause a desired reaction using such a stable chemical species as it is as a reagent. Further, it is not favorable in terms of management of the reagent that the composition of the solution system changes with the progress of the dimerization during the long-term storage. Moreover, it is not always easy operation to heat the reagent with the addition of the acid even though the dimer can be converted back to the original aldehyde by such operation. It is desirable to use the hemiacetal as it is as the reagent, if possible, without any specific pretreatment in view of the fact that the hemiacetal originally has sufficient reactivity.

As explained above, an effective method has been demanded to preserve 2,2-difluoroacetaldehyde in hemiacetal form with improved preservation stability.

The gradual formation of such a dimer compound is not significantly observed in the case where 2,2,2-trifluoroacetaldehyde (represented by the following formula (a)), which is analogous in structure to the target 2,2-difluoroacetaldehyde of the present invention, is converted to a hemiacetal (represented by the following formula (b)).

In the above formulas, $R^2$ represents a $C_1$-$C_6$ linear, branched or cyclic hydrocarbon group in which a part or all of hydrogen atoms may be substituted with a fluorine atom.

In order words, the dimer formation is a phenomenon (problem) peculiar to the 2,2-difluoroacetaldehyde hemiacetal.

Means for Solving the Problems

The present inventors have made extensive researches to solve the foregoing problems and have resultantly found that it is possible to solve the foregoing problems by: allowing a hemiacetal of the formula (3), which is formed between 2,2-difluoroacetaldehyde and an alcohol of the formula (2), to coexist with an excessive amount of the alcohol of the formula (2), thereby providing a "2,2-difluoroacetaldehyde-alcohol composite system"; controlling the pH of the "2,2-difluoroacetaldehyde-alcohol composite" to be substantially neutral; controlling the water content of the "2,2-difluoroacetaldehyde-alcohol composite system" to 1000 ppm or lower; and controlling the total molar amount of the alcohol of the formula (2) (i.e. the total molar amount of "free alcohol" and "2,2-difluoroacetaldehyde hemiacetal"; the same applies to the following) to be 1.15 to 4.00 times the total molar amount of the "2,2-difluoroacetaldehyde" (i.e. the total molar amount of "free 2,2-difluoroacetaldehyde" and "2,2-difluoroacetaldehyde hemiacetal"; the same applies to the following).

In the above formulas, $R^2$ represents a $C_1$-$C_6$ linear, branched or cyclic hydrocarbon group in which a part or all of hydrogen atoms may be substituted with a fluorine atom.

When the "2,2-difluoroacetaldehyde-alcohol composite system" is controlled such that: the pH of the "2,2-difluoroacetaldehyde-alcohol composite system" is substantially neutral; the water content of the "2,2-difluoroacetaldehyde-alcohol composite system" is 1000 ppm or lower; and the total molar amount of the alcohol of the formula (2) is 1.15 to 4.00 times the total molar amount of the "2,2-difluoroacetaldehyde", the hemiacetal of the formula (3) becomes a main component in the system.

  (3)

In the formula (3), $R^2$ has the same definition as in the formula (2).

Under the above conditions, there are detected almost no free 2,2-difluoroacetaldehyde and almost no "acetal" in which two alcohol molecules are bound to 2,2-difluoroacetaldehyde. Namely, the hemiacetal and the excess free alcohol coexist as main components in the system.

In particular, the present inventors have surprisingly found a peculiar phenomenon in which the formation of the "dimer" is significantly less likely to occur when the total molar amount of the alcohol in the system is 1.15 times or more whereas it is not possible to suppress the gradual formation of the "dimer" when the total molar amount of the alcohol in the system is less than 1.15 times. In other words, the present inventors have found that the hemiacetal of the formula (3) is likely to exist stably under this composition condition.

As in the after-mentioned synthesis examples, an α,α-difluoroacetate of the following formula can be used as a raw material for synthesis of 2,2-difluoroacetaldehyde.

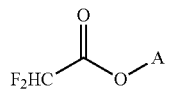

In the above formula, A represents a $C_1$-$C_6$ linear, branched or cyclic hydrocarbon group in which a part or all of hydrogen atoms may be substituted with a fluorine atom. When the α,α-difluoroacetate is subjected to partial reduction, 2,2-difluoroacetaldehyde is formed as a reaction product with the ester moiety (—O-A) of the α,α-difluoroacetate left as it is so as to correspond to the moiety (—O—$R^2$) of the 2,2-difluoroacetaldehyde hemiacetal. (In the case where the reduction reaction is carried out in an alcohol solvent, there occurs ester interchange in a part of the ester moiety. Even in such a case, the total amount of the alcohol in the system does not change.) After the aldehyde is converted to the hemiacetal, the moiety (—O—$R^2$) of the hemiacetal is counted as the total alcohol amount (because this moiety has the ability of generating an alcohol by decomposition). With attention focused only on the chemical species "2,2-difluoroacetaldehyde hemiacetal", the ratio of the aldehyde to the alcohol in the compound is exactly 1:1 irrespective of their origins. Namely, the amount of the alcohol is exactly 1 mol (1 molar time) per 1 mol of the aldehyde.

When the "2,2-difluoroacetaldehyde hemiacetal" is formed using the α,α-difluoroacetate as the starting raw material, the alcohol moiety derived from the raw material is already present in an amount of 1 molar time relative to the aldehyde in the resulting reaction solution. After all, the expression "the total amount of the alcohol in the system is 1.15 to 4.00 mol per 1 mol of the aldehyde" means that the amount of the free alcohol, except the hemiacetal-forming alcohol component, is 15 to 300% based on the amount of the aldehyde in the present invention. It is assumed that, for some reason, the dimer formation is prevented by the coexistence of a small amount of the free alcohol in the system. Although details of the dimer formation prevention mechanism are unknown, it is possible based on these findings to achieve stable long-term preservation of 2,2-difluoroacetaldehyde in the form of the hemiacetal of the formula (3).

In the present invention, $R^2$ of the hemiacetal of the formula (3) and $R^2$ of the alcohol of the formula (2) have the same definition. Within the range of this definition, $R^2$ of the hemiacetal of the formula (3) and $R^2$ of the alcohol of the formula (2) may be the same group or different groups. There would be no problem even when each of the hemiacetal of the formula (3) and the alcohol of the formula (2) is a mixture of chemical species with two or more kinds of $R^2$ (see the after-mentioned examples).

It is herein noted that, in the present invention, the state where the hemiacetal of the formula (3) is stably preserved is expressed as "improvement of the preservation stability of 2,2-difluoroacetaldehyde".

Accordingly, the present invention provides a method for improving preservation stability of 2,2-difluoroacetaldehyde, comprising:

a first step of forming a "2,2-difluoroacetaldehyde-alcohol composite system" that contains a hemiacetal of the 2,2-difluoroacetaldehyde as represented by the formula (3) and a free alcohol as represented by the formula (2)

where $R^2$ represents a $C_1$-$C_6$ linear, branched or cyclic hydrocarbon group in which a part or all of hydrogen atoms may be substituted with a fluorine atom

where $R^2$ has the same definition as in the formula (3); and a second step of storing the "2,2-difluoroacetaldehyde-alcohol composite system" in a storage container, wherein, at the initiation of storage of the "2,2-difluoroacetaldehyde-alcohol composite system" in the storage container, the "2,2-difluoroacetaldehyde-alcohol composite system" has a substantially neutral pH and a water content of 1000 ppm or lower; and wherein, at the initiation of storage of the "2,2-difluoroacetaldehyde-alcohol composite system" in the storage container, the total molar amount of the alcohol (present as "free alcohol" and as "2,2-difluoroacetaldehyde hemiacetal"; the same applies to the following) in the composite system is 1.15 to 4.00 times the total molar amount of the 2,2-difluoroacetaldehyde (present as "free aldehyde" and as "2,2-difluoroacetaldehyde hemiacetal"; the same applies to the following).

Effects of the Invention

In the present invention, it is possible to preserve 2,2-difluoroacetaldehyde, which is useful as an intermediate for production of pharmaceutical and agrichemical products etc., in hemiacetal form stably for a long term, i.e., possible by easy operation to suppress gradual changes of solution composition caused by the formation of the dimer.

DETAILED DESCRIPTION OF THE EMBODIMENTS

Hereinafter, the respective features of the present invention will be described below in detail. It should be understood that various and variations of the following embodiments can be made based on the general knowledge of those skilled in the art without departing from the scope of the present invention.

As mentioned above, the preservation stability improvement method of the present invention includes the following two steps:

first step: allowing the 2,2-difluoroacetaldehyde to coexist with the alcohol of the formula (2), thereby forming the "2,2-difluoroacetaldehyde-alcohol composite system" that contains the hemiacetal of the formula (3); and second step: storing the "2,2-difluoroacetaldehyde-alcohol composite system" in the storage container.

The respective steps will be explained in detail below.

[1] First Step

The first step is a step of forming the "2,2-difluoroacetaldehyde-alcohol composite system".

[Amount of Alcohol]

In the present invention, the "2,2-difluoroacetaldehyde-alcohol composite system" refers to a composite system (composition) in which the alcohol of the formula (2) is present as excess alcohol separately from the 2,2-difluoroacetaldehyde hemiacetal of the formula (3). In this composite system, the total amount of the alcohol of the formula (2) is 1.15 to 4.00 molar times relative to the total amount of the 2,2-difluoroacetaldehyde.

The alcohol of the formula (2) may be of a single kind of alcohol or a mixture of two or more kinds of alcohols. In the latter case, the total amount of the two or more kinds of the alcohols is 1.15 to 4.00 molar times relative to the total amount of the 2,2-difluoroacetaldehyde.

Under this condition, the 2,2-difluoroacetaldehyde is converted to the hemiacetal of the formula (3) with virtually no conversion to acetal form. The hemiacetal and the excess free alcohol coexist as main components in the system. Depending on the conditions of post treatment after the reaction, a part of the hemiacetal may be converted to the dimer of the formula (4). The dimer is present in a very small amount at the initiation of the storage.

Even when the total amount of the alcohol exceeds 2.00 molar times relative to the total amount of the 2,2-difluoroacetaldehyde, it is less likely that the stability of the 2,2-difluoroacetaldehyde could be further improved by the presence of such an excess amount of the alcohol. It is possible to achieve the object of the present invention, i.e., improve the preservation stability of the 2,2-difluoroacetaldehyde, while maintaining the original aldehyde activity of the 2,2-difluoroacetaldehyde, with almost no conversion to acetal form even when the total amount of the alcohol exceeds 2.00 molar times relative to the total amount of the 2,2-difluoroacetaldehyde. It is however wasteful to use the alcohol in too much amount. Thus, the total amount of the alcohol is preferably 1.15 to 2.00 molar times, more preferably 1.15 to 1.60 molar times, still more preferably 1.15 to 1.30 molar times, relative to the total amount of the 2,2-difluoroacetaldehyde. The use of such a small excessive amount of the alcohol (e.g. the presence of 15 to 30% of the free alcohol) is economically most advantageous as well as makes it possible to ensure the preservation stability of 2,2-difluoroacetaldehyde.

In the first step, there is no particular limitation on the method for forming the "2,2-difluoroacetaldehyde-alcohol composite system" as long as the 2,2-difluoroacetaldehyde hemiacetal of the formula (3) is allowed to coexist with the excessive amount of the alcohol of the formula (2).

It is feasible to obtain the composite system by mixing a simple substance of the 2,2-difluoroacetaldehyde with a simple substance of the alcohol of the formula (2) or by synthesizing the 2,2-difluoroacetaldehyde in a solvent other than alcohol and then substituting the solvent of the resulting reaction solution with the alcohol of the formula (2). It is alternatively feasible to obtain the composite system by synthesizing the 2,2-difluoroacetaldehyde in a solvent containing the alcohol and allowing the excess alcohol to remain in the system.

As mentioned above, when the 2,2-difluoroacetaldehyde hemiacetal is formed using the α,α-difluoroacetate as the starting raw material, the alcohol moiety ($-OR^2$) derived from the raw material is already present in an amount of 1 molar time (i.e. in an equimolar amount) relative to the aldehyde in the resulting reaction solution. It is feasible to obtain the 2,2-difluoroacetaldehyde-alcohol composite system by adding the excess alcohol to this reaction solution.

[Solution pH]

In the present invention, the pH of the "2,2-difluoroacetaldehyde-alcohol composite system" needs to be substantially neutral at the supply of the "2,2-difluoroacetaldehyde-alcohol composite system" to the storage container. The expression "substantially neutral" means that the sample solution has a pH of 5 to 10 (regarded as "near neutral pH" on the basis of common sense of those skilled in the art), more preferably a pH of 6 to 9, as determined by dipping a pH paper in the sample solution. When the pH of the composite system falls out of this range and shifts to an acidic side, the hemiacetal component may be unfavorably decomposed by an acid. When the pH of the composite system falls out of this range and shifts to an alkaline side, there is likely to occur a side reaction such as Cannizzaro reaction so that it becomes unfavorably difficult to stabilize the 2,2-difluoroacetaldehyde as intended by the present invention.

[Water Content]

Further, the water content of the "2,2-difluoroacetaldehyde-alcohol composite system" needs to be 1000 ppm or lower (based on the total solution mass of the "2,2-difluoroacetaldehyde-alcohol composite system) in the present invention. When the water content of the composite system is higher than the above range, the following hydrate is generated by reaction of the 2,2-difluoroacetaldehyde with water.

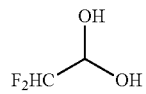

The hydrate is however a not-so-stable chemical species. The nucleophilic reaction conditions against a carbonyl group are limited when the hydrate is handled in aqueous solution form. Further, the hydrate is unfavorable in that the reactivity of the hydrate is lower than the reactivity of the "2,2-difluoroacetaldehyde-alcohol composite system". Although the hydrate can be converted to a hemiacetal, it is necessary for such conversion reaction to perform dehydration on the system in which the excessive alcohol is present. This leads to complicated operation. For these reasons, the water content of the composite system is preferably 500 ppm or lower, more preferably 200 ppm or lower. The dehydration (water content reduction) can be performed with the use of a dehydration agent (such as anhydrous metal salt e.g. magnesium chloride or calcium chloride, zeolite or the like). Alternatively, the dehydration can be performed by concentration/solvent substitution using evaporation. It is more effective to perform the dehydration by combination of these multiple techniques.

[Method 1 for Synthesis of 2,2-Difluoroacetaldehyde]

As is commonly known, it is feasible to obtain 2,2-difluoroacetaldehyde as the hemiacetal of the formula (3) by partial reduction of an α,α-difluoroacetate of the following formula (where the moiety (—O-A) corresponds to (—O—R²)) with a hydride reduction agent such as lithium aluminum hydride or sodium borohydride as described in Non-Patent Document 1.

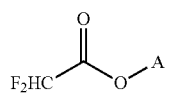

In the above formula, A represents a $C_1$-$C_6$ linear, branched or cyclic hydrocarbon group in which a part or all of hydrogen atoms may be substituted with a fluorine atom. There can suitably be used an ethyl group or a methyl group as A.

The reduction reaction is preferably carried out in an anhydrous ether solvent at a temperature of preferably −70° C. to −100° C. as in the after-mentioned synthesis example 1. The generation of 2,2-difluoroethanol as an over-reduction product can be suppressed by such low-temperature reaction.

The 2,2-difluoroethanol generated as the over-reduction product belongs to the alcohol of the formula (2) and forms a hemiacetal with the 2,2-difluoroacetaldehyde obtained as the target compound (also referred to as "DFAL-DFOL"). In this case, the moiety (—O—CH$_2$—CHF$_2$) corresponds to (—O—R²). It can thus be said that the 2,2-difluoroethanol also contributes to stabilization of the 2,2-difluoroacetaldehyde. It is often the case that, even when the solvent of the system is substituted by evaporation with the addition of excess ethanol to the system during the after-mentioned post treatment, the DFAL-DFOL remains in the system (see the after-mentioned examples). Consequently, there often coexist two or more kinds of hemiacetals in the system.

However, the yield of the 2,2-difluoroacetaldehyde in the hydride reduction reaction is lowered when the 2,2-difluoroethanol is generated during the reduction reaction. The preservation stability of the 2,2-difluoroacetaldehyde is sufficiently improved even by the coexistence of a less expensive unsubstituted alcohol. Thus, the necessity for generating very expensive 2,2-difluoroethanol as the by-product of the reduction reaction for stabilization of the 2,2-difluoroacetaldehyde is low. In the case of reducing the α,α-difluoroacetate with lithium aluminum hydrate etc., it is preferable to minimize the over-reduction by setting the reaction temperature to a lower level (e.g. −70 to −100° C.) or by gradually mixing the reagent (while controlling the temperature).

Since the resulting reaction solution is strongly basic, it is preferable to bring the reaction solution into contact with ice water, neutralize the reaction solution with an acid and thereby control the reaction solution to a substantially neutral pH (as defined above) immediately after the completion of the reaction. More specifically, the neutralization is performed with the addition of the acid until the pH of the reaction solution becomes 5 to 10 (preferably 6 to 9) as mentioned above. In order to prevent the reaction solution from exceeding a neutralization point and shifting to an acidic side, the acid used for the neutralization is preferably a weak acid such as acetic acid, carbonic acid or boric acid (particularly preferably acetic acid). A judgment as to whether the pH of the reaction solution becomes substantially neutral can be made by sampling the reaction solution and dipping a commercially available pH paper in the sample solution.

Then, the alcohol of the formula (2) (e.g. ethanol) is added to the substantially neutralized reaction solution so that the hemiacetal is converted to that between the aldehyde and the last added alcohol. This operation is however not essential (because the stability of the 2,2-difluoroacetaldehyde is improved even when the system is in the form of a composite solution in which two or more kinds of hemiacetals are present).

The reaction solution is subjected to extraction with an water-insoluble organic solvent (such as diethyl ether). By this extraction, the hemiacetal is extracted as an organic layer while an water-soluble substance contained in a large amount in the reaction solution after the hydride reduction reaction is separated and removed as an aqueous phase. The water content of the reaction solution is controlled to 1000 ppm or lower by drying the organic phase (removing water) with a drying agent and then subjecting the organic phase to solvent distillation by evaporation. The hemiacetal of the formula (3) (1-alkoxy-2,2-difluoroethanol) is obtained by the above post treatment operations. However, there is almost no excess alcohol coexisting with the hemiacetal because the hemiacetal undergoes solvent extraction in the post treatment process. In this state, it is not possible to achieve the object of the present invention, that is, long-term improvement of the preservation stability of the target aldehyde. In the present invention, this product needs to be converted to the above-specified "2,2-difluoroacetaldehyde-alcohol composite system". The alcohol of the formula (2) is thus added to the hemiacetal such that the total amount of the alcohol of the formula (2) is 1.15 to 4.00 molar times relative to the total amount of the 2,2-difluoroacetaldehyde. After the addition of the alcohol, the composite system may be subjected to evaporation to not only remove water but also let the alcohol remain in a small excess amount of 1.15 to 4.00 molar times (i.e. very effective amount for improvement of preservation stability) remain in the system and recover the reminder of the alcohol.

The distillation of the water-insoluble organic solvent may be performed simultaneously with the distillation of the alcohol by, immediately after extracting the acetal into the water-insoluble organic solvent and dehydrating the extract solution with the dehydration agent, excessively adding the alcohol of the formula (2) to the dehydrated solution and then evaporating the resulting solution.

In the case where the removal of a high-boiling component is desired, distillation may be performed under high vacuum degree, separately from the distillation of the alcohol, so as to recover the hemiacetal as a fraction. In this case, it is convenient to perform the distillation with a not-so-large plate number so that both of the hemiacetal and the excess alcohol can be recovered simultaneously (i.e. the "2,2-difluoroacetaldehyde-alcohol composite system" can be temporarily recovered as a fraction).

As the alcohol of the formula (2), a $C_1$-$C_6$ unsubstituted alcohol is preferably used because of its low cost and sufficient stabilization effect. Among others, methanol and ethanol are particularly preferred because each of methanol and ethanol is readily available as a dehydrated reagent on a large scale and shows a large stabilization effect.

[Method 2 for Synthesis of 2,2-Difluoroacetaldehyde]

It is alternatively feasible to obtain 2,2-difluoroacetaldehyde by contact of an α,α-difluoroacetate (i.e. the same raw material as that of the above synthesis method 1) and hydrogen ($H_2$) gas in the presence of a specific ruthenium complex as a catalyst (as described in Patent Document 3) (see the after-mentioned synthesis example 2). This method is particularly advantageous for large-scale synthesis because the direct catalytic reaction between the α,α-difluoroacetate and the hydrogen gas needs the ruthenium complex as the catalyst but does not need to use a hydride reduction agent difficult to handle in a large amount.

As the ruthenium catalyst, a complex of the following formula is usable in the catalytic reaction.

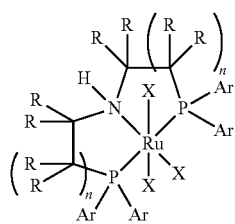

In the above formula, R each independently represents a hydrogen atom, an alkyl group, a substituted alkyl group, an aromatic group or a substituted aromatic group; Ar each independently represents an aromatic group or a substituted aromatic group; X each independently represents a ligand with a formal charge of −1 or 0 (with the proviso that the sum of the formal charges of three X is −2); and n each independently represent an integer of 1 or 2.

Examples of the substituted alkyl and aromatic groups are those obtained by substitution of any number of and any combination of substituents onto any of carbon atoms of the alkyl and aromatic groups. As such substituents, there can be used: halogen atoms such as fluorine, chlorine and bromine; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; cyano group; lower alkoxycarbonyl groups such as methoxycarbonyl, ethoxycarbonyl and propoxycarbonyl; aromatic-ring groups such as phenyl, naphthyl, anthryl, pyrrolyl (including nitrogen-protected form), pyridyl, furyl, thienyl, indolyl (including nitrogen-protected form), quinolyl, benzofuryl and benzothienyl; carboxyl group; protected carboxyl groups; amino group; protected amino groups; hydroxyl group; and protected hydroxyl groups. In the substituted alkyl group, an arbitrary carbon-carbon single bond or bonds may be replaced by any number of and any combination of carbon-carbon double bonds and carbon-carbon triple bonds. (As a matter of course, the alkyl group with such an unsaturated bond or bonds may have any of the above substituents.) Depending on the kind of the substituent, the substituent itself may be involved in a side reaction. However, the side reaction can be minimized by the adoption of suitable reaction conditions. In the present specification, the term "lower" means that the group to which the term is attached has 1 to 6 carbon atoms in the form of a linear structure, a branched structure or a cyclic structure (in the case of 3 or more carbons). The aromatic ring groups described above as "such substituents" may further be substituted with a halogen atom, lower alkyl group, lower haloalkyl group, lower alkoxy group, lower haloalkoxy group, cyano group, lower alkoxycarbonyl group, carboxyl group, protected carboxyl group, amino group, protected amino group, hydroxyl group, protected hydroxyl group etc. As the protecting groups of the pyrrolyl, indolyl, carboxyl, amino and hydroxyl groups, there can be used those described in "Protective Groups in Organic Synthesis", Third Edition, 1999, John Wiley & Sons, Inc.

Among others, a ruthenium complex of the following formula (available as Ru-MACHO™) is particularly preferred because of its high activity.

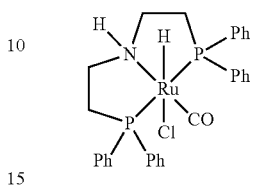

In the above formula, Ph represents a phenyl group.

The ruthenium complex can be prepared in a similar manner with reference to the preparation technique of Ru-MACHO™. Further, the ruthenium complex can be used even when water or organic solvent such as toluene is contained in the ruthenium complex. In this case, it suffices that the purity of the ruthenium complex is 70% or higher. The purity of the ruthenium complex is preferably 80% or higher, more preferably 90% or higher.

It suffices to use the ruthenium complex in an amount of 0.000001 mol or more per 1 mol of the α,α-difluoroacetate used as the raw material. The amount of the ruthenium complex used is preferably 0.00001 to 0.005 mol, more preferably 0.00002 to 0.002 mol, per 1 mol of the α,α-difluoroacetate.

Although the catalytic reduction reaction needs to be carried out in the presence of a base, it is alternatively feasible to carry out the catalytic reduction reaction in the absence of the base in the case where at least one of three X ligands of the ruthenium complex is $BH_4$.

Examples of the base are: alkali metal hydrogencarbonates such as lithium hydrogencarbonate, sodium hydrogencarbonate and potassium hydrogencarbonate; alkali metal carbonates such as lithium carbonate, sodium carbonate and potassium carbonate; alkali metal hydroxides such as lithium hydroxide, sodium hydroxide and potassium hydroxide; tetraalkyl ammonium hydroxides such as tetramethyl ammonium hydroxide, tetraethyl ammonium hydroxide, tetra-n-propyl ammonium hydroxide and tetra-n-butyl ammonium hydroxide; alkali metal alkoxides such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide; organic bases such as triethylamine, diisopropylethylamine, 4-dimethylaminopyridine and 1,8-diazabicyclo[5.4.0]undec-7-ene; alkali metal bis(trialkylsilyl)amides such as lithium bis(trialkylsilyl)amide, sodium bis(trialkylsilyl)amide and potassium bis(trialkylsilyl)amide; and alkali metal borohydrides such as lithium borohydride, sodium borohydride and potassium borohydride. Among others, alkali metal alkoxides (whose carbon number is 1 to 6) are preferred. Particularly preferred are lithium methoxide, sodium methoxide and potassium methoxide. In general, sodium methoxide is available in the form of a methanol solution as in the after-mentioned synthesis example. In the case of using such a methanol solution of sodium methoxide, methanol remains in the reaction system (that is, acts as at least a part of the alcohol of the formula (2)).

It suffices to use the base in an amount of 0.001 mol or more per 1 mol of the α,α-difluoroacetate used as the raw material. The amount of the base used is preferably 0.005 to 5 mol, more preferably 0.01 to 3 mol, per 1 mol of the α,α-difluoroacetate.

It suffices to use the hydrogen gas in an amount of 1 mol or more per 1 mol of the α,α-difluoroacetate. The hydrogen gas is preferably used in a large excessive amount, more preferably in a largely excessive amount under pressurized conditions.

There is no particular limitation on the hydrogen gas pressure. The hydrogen gas pressure is preferably 2 to 0.001 MPa, more preferably 1 to 0.01 MPa.

Examples of the reaction solvent are: aliphatic hydrocarbon solvents such as n-hexane, cyclohexane and n-heptane; aromatic hydrocarbon solvents such as toluene, xylene and mesitylene; halogenated solvents such as methylene chloride, 1,2-dichloroethane and α,α,α-trifluorotoluene; ether solvents such as diethyl ether, 1,2-dimethoxyethane, 1,4-dioxane, tetrahydrofuran, 2-methyltetrahydrofuran, tert-butyl methyl ether, diisopropyl ether, diethylene glycol dimethyl ether and anisole; alcohol solvents such as methanol, ethanol, n-propanol, isopropanol, n-butanol, tert-butanol, n-pentanol, n-hexanol and cyclohexanol; amide solvents such as N,N-dimethylformamide, N,N-dimethylacetamide and 1,3-dimethyl-2-imidazolidinone; nitrile solvents such as acetonitrile, propionitrile and benzonitrile; dimethyl sulfoxide; and water. Among others, aliphatic hydrocarbon solvents, aromatic hydrocarbon solvents, halogenated solvents, ether solvents and alcohol solvents are preferred. Particularly preferred are aliphatic hydrocarbon solvents, aromatic hydrocarbon solvents, ether solvents and alcohol solvents. These reaction solvents can be used solely or in combination of two or more thereof.

The alcohol reaction solvent (hereinafter referred to as "solvent A") has the effect of increasing the reaction rate, whereas each of the aliphatic hydrocarbon solvent, aromatic hydrocarbon solvent, halogenated solvent and ether solvent (hereinafter referred to as "solvent B") has the effect of suppressing the over-reduction of the raw material to β,β-difluoroethanol. In order to maximize the utility of the present invention, it is a preferred embodiment (as embodiment 1) to use a mixture of the solvent A and the solvent B. In this case, it suffices that the volume ratio of these solvents (A:B assuming the sum of A and B as 100) is 60 or more:40 or less. The volume ratio A:B is preferably 70 or more:30 or less, more preferably 80 or more:20 or less.

Further, it suffices to use the reaction solvent in an amount of 0.03 L (liter) or more per 1 mol of the α,α-difluoroacetate used as the raw material. The amount of the reaction solvent used is preferably 0.05 to 10 L, more preferably 0.07 to 7 L, per 1 mol of the α,α-difluoroacetate.

In the case of using the alcohol solvent as the reaction solvent, the reaction temperature is generally +30° C. or lower, preferably +25 to −50° C., more preferably +20 to −40° C., still more preferably +15 to −30° C. In the case of using the aliphatic hydrocarbon solvent, aromatic hydrocarbon solvent, halogenated solvent or ether solvent as the reaction solvent, the reaction temperature is generally +50° C. or lower, preferably +45 to −30° C., more preferably +40 to −20° C., still more preferably +35 to −10° C. In the case of using the mixed solvent of two or more reaction solvents, the reaction temperature can be set to the above temperature range with respect to the reaction solvent present in the greatest amount.

In order to maximize the utility of the present invention, it is particularly preferable to carry out the reaction in the alcohol solvent under temperature conditions of 20° C. or lower or carry out the reaction in the aliphatic hydrocarbon solvent, aromatic hydrocarbon solvent, halogenated solvent or ether solvent under reaction temperatures of 40° C. or lower.

It is unfavorable to carry out the reaction under temperature conditions exceeding the above temperature range because it is likely that, under such high temperature condition, the over-reduction will proceed to cause an increase in the selectivity of the 2,2-difluoroethanol and a decrease in the yield of the target compound.

In either case, the target 2,2-difluoroacetaldehyde is obtained with a high yield under much higher reaction conditions (i.e. moderate temperature conditions near room temperature) by the reduction reaction using the ruthenium catalyst than by the reduction reaction using the hydride reduction agent (see above).

Furthermore, it suffices that the reaction time is 72 hours or less. As the reaction time varies depending on the raw substrate material and reaction conditions, it is preferable to determine the time at which there is seen almost no decrease of the raw substrate material as the end of the reaction while monitoring the progress of the reaction by any analytical means such as gas chromatography, liquid chromatography or nuclear magnetic resonance.

In principle, the post treatment process after the catalytic reduction reaction is the same as the post treatment process after the hydride reduction reaction. Namely, the basic reaction solution is first neutralized with an acid (preferably an weak acid). The alcohol of the formula (2) (such as ethanol) is then added to the reaction solution, so that the 2,2-difluoroacetaldehyde obtained as the reaction product is converted to its corresponding hemiacetal. Subsequently, the reaction solution is subjected to extraction with an water-insoluble organic solvent so as to extract the hemiacetal as an organic phase. The water content of the reaction solution is controlled to 1000 ppm or lower by drying the organic phase (removing water) with a drying agent and then subjecting the organic phase to solvent distillation by evaporation. By these operations, the hemiacetal of the formula (3) (1-alkoxy-2,2-difluoroethanol) is obtained. The "2,2-difluoroacetaldehyde-alcohol composite system" is provided with the addition of the excess alcohol to the hemiacetal.

Alternatively, the composite system may be provided by extracting the hemiacetal into the water-insoluble organic solvent, drying the extract solution with the drying agent, adding the excess alcohol to the dried solution and then evaporating the water-insoluble organic solvent.

In the case of using a metal alcoholate as the base in the reduction reaction, the post treatment process can be performed in an easier manner than the above. More specifically, the reaction solution is first neutralized to a substantially neutral pH with the addition of a "water-free acid" such as glacial acetic acid or acetic anhydride. When the metal alcoholate is used as the base, the alcohol of the formula (2) is solely generated as a by-product (water is not generated as a by-product) in the neutralization of the acid and the base. There is no need to separately perform solvent extraction as long as the reaction solution is subjected to any treatment for separation of by-produced salt. The reaction solution is in a state where the alcohol of the formula (2) is already present, along with the solvent (generally, alcohol) in which the metal alkoxide has been dissolved, in the system. It is thus feasible to perform ordinary distillation on the reaction solution. The distillation may be performed to distill out the low-boiling free alcohol or to obtain the "2,2-difluoroacetaldehyde-alcohol composite system" of the present invention as a fraction for the purpose of removing the high-boiling component. As required, the thus-obtained fraction may be repeatedly treated by further adding the alcohol of the formula (2) and concentrating the resulting fraction. By such treatment operation, both of the low-boiling component and the high-boiling component are removed so that there is obtained the "2,2-difluoroacetaldehyde-alcohol composite system" with high quality. Even in the case of adopting the above post-treatment process, there would be no problem in further reducing the water content of the composite system by appropriately bringing the composite system into contact with a drying agent.

As the alcohol of the formula (2), a $C_1$-$C_6$ unsubstituted alcohol is preferably used because of its low cost and sufficient stabilization effect. Among others, methanol and ethanol are particularly preferred because each of methanol and ethanol is readily available as a dehydrated reagent on a large scale and shows a large stabilization effect.

[Method for Determination of Solution Composition]

Regardless of whether the 2,2-difluoroacetaldehyde is synthesized by either of the above synthesis methods, it is preferable to determine the composition of the reaction solution at the supply of the reaction solution into the storage container during or after the post treatment process. Although there is no particular limitation on the method for determining the composition of the reaction solution, $^1$H-NMR is a particularly effective technique for determining the composition of the reaction solution. Depending on the kind of the chemical species, there is a case that the composition of the reaction solution can be determined more accurately by $^{19}$F-NMR (see, for example, quantification analysis of DFAL-DFOL as in the after-mentioned examples). It is thus effective to use $^1$H-NMR as a basic technique optionally in combination with $^{19}$F-NMR.

More specifically, the peaks of the respective compounds (free alcohol, hemiacetal and dimer) are identified based on the chemical shifts of proton or fluorine in the NMR spectrum. By comparison of the peaks of the respective compounds with the peak of internal standard substance in consideration of the number of protons in each compound, the mole numbers of the chemical species are determined in a short time. The ratio of the total mole number of the 2,2-difluoroacetaldehyde to the total mole number of the alcohol is calculated based on these composition determination results.

By this analysis, it becomes easier to judge the amount of the alcohol to be further added. The alcohol is preferably immediately added when the total amount of the alcohol has not reached the predetermined amount in the present invention. When the alcohol is contained in too much amount, by contrast, the alcohol is removed by evaporation.

[2] Second Step

The second step is a step of storing, in the storage container, the "2,2-difluoroacetaldehyde-alcohol composite system" formed in the first step.

As mentioned above, the "2,2-difluoroacetaldehyde-alcohol composite system" needs to satisfy the following conditions at the initiation of the storage: (a) the composite system has a substantially neutral pH; (b) the composite system has a water content of 1000 ppm or lower; and (c) the total molar amount of the alcohol (i.e. the total molar amount of "free alcohol" and various forms of "2,2-difluoroacetaldehyde hemiacetal") is 1.15 to 4.00 times the total molar amount of the 2,2-difluoroacetaldehyde (i.e. the total molar amount of "free 2,2-difluoroacetaldehyde" and various forms of "2,2-difluoroacetaldehyde hemiacetal"). The "2,2-difluoroacetaldehyde-alcohol composite system" satisfying these conditions is stored in the storage container.

In the second step, it is most common to introduce the above-formed "2,2-difluoroacetaldehyde-alcohol composite system" into the storage container. However, the method of the present invention does not exclude the case of first putting a simple substance of the 2,2-difluoroacetaldehyde hemiacetal into the storage container, adding the free alcohol in a predetermined amount into the storage container and thereby forming the "2,2-difluoroacetaldehyde-alcohol composite system" within the storage container, or conversely first placing the free alcohol in the storage container and then adding a simple substance of the 2,2-difluoroacetaldehyde hemiacetal into the storage container (i.e. the case where the first and second steps are conducted simultaneously).

As already mentioned above, the hydrate is generated by reaction of the 2,2-difluoroacetaldehyde with water. The hydrate is a not-so-stable chemical species and is significantly lower in reactivity than "2,2-difluoroacetaldehyde-alcohol composite system". The reaction conditions are limited by the handling of the hydrate in aqueous solution form. It is thus preferable to store "2,2-difluoroacetaldehyde-alcohol composite system" in the closed container so that the composite system does not absorb moisture in the air.

The composite system may be managed by the coexistence of a dehydration agent or by the addition of an inert gas such as nitrogen or argon. However, such strict management is normally not required because the "2,2-difluoroacetaldehyde-alcohol composite system" of the present invention is sufficiently high in stability.

The "2,2-difluoroacetaldehyde-alcohol composite system" can suitably be stored in either a glass container (including a container with a glass lining) or a stainless steel container.

There is no particular limitation on the storage temperature. The composite system can be stored in a wide temperature range of −40 to +70° C. The storage temperature is preferably −30 to +50° C., more preferably at around room temperature (more specifically 10 to 45° C., particularly preferably 20 to 35° C.). The higher the storage temperature, the more the formation of the dimer may be suppressed. In view of overall material stability, it is most preferable to store the composite system at around room temperature in an environment less likely to be exposed to light. This will not be a hindrance to transportation of the composite system in the state of being stored in the storage container. A problem would not immediately arise even when the composite system is temporarily exposed to temperature conditions out of the above temperature range.

In the case where the composite system is stored for a long term, it is preferable to again sample the solution and measure the composition of the sampled solution immediately before use as a reagent. However, the "2,2-difluoroacetaldehyde-alcohol composite system" stored by the method of the present invention is unlikely to cause a significant composition change relative to that at the initiation of the storage and is easily able to maintain high activity as the aldehyde reagent as already mentioned above. Thus, the composite system can be directly used as it is for reaction.

EXAMPLES

The present invention will be described in more detail below by way of the following examples. It should however be understood that the following examples are not intended to limit the present invention thereto.

[Synthesis Example 1] Synthesis of DFAL-EtOH

In 30 mL of diethyl ether, 2.5 g (20 mmol) of ethyl α,α-difluoroacetate ($CHF_2COOC_2H_5$) was dissolved. Into this solution, 1.9 g (50 mmol) of aluminum lithium hydride cooled to −78° C. and 50 mL of tetrahydrofuran solution were dropped. The solution was stirred for 3 hours, followed by adding thereto 5 mL of ethanol and heating to room temperature. Into the resulting reaction solution, ice water was poured. Further, 15 mL of concentrated sulfuric acid was added to the reaction solution. The reaction solution was then subjected to extraction with diethyl ether. After the organic phase was dried with anhydrous magnesium sulfate, the organic phase was subjected to distillation purification to distill therefrom diethyl ether. As a result, 1-ethoxy-2,2-difluoroethanol (DFAL-EtOH) was obtained with a yield of 60%.

[Synthesis Example 2] Synthesis of DFAL-EtOH

Into an autoclave reactor of stainless steel, 450 g (3.6 mol) of ethyl α,α-difluoroacetate ($CHF_2COOC_2H_5$), 470 mg (730 mmol) of the following ruthenium complex, 170 g of 28% sodium methoxide methanol solution (containing 910 mmol of sodium methoxide) and 1.2 L of methanol were put.

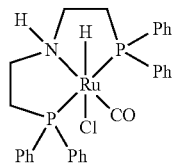

The inside of the reactor was replaced five times with hydrogen gas. The hydrogen pressure inside the reactor was set to 1.0 MPa. Then, the content of the reactor was reacted with stirring for 8 hours at 15° C. After the completion of the reaction, it was confirmed by $^{19}$F-NMR analysis that: the conversion rate of methyl α,α-difluoroacetate was 40%; and the selectivity of DFAL-hemiacetal (the sum of methyl hemiacetal and ethyl hemiacetal) was 95%. In the $^{19}$F-NMR analysis, quantification was performed using α,α,α-trifluorotoluene as internal standard substance.

With the addition of 51.9 g (860 mmol) of acetic acid, the reaction completed solution was changed to a pH of 8. Thus, the pH of the reaction completed solution was considered as becoming substantially neutral. The addition of the acetic acid was stopped. This solution was directly subjected to distillation (bottom temperature: ~66° C., vacuum degree: ~2.1 kPa), thereby obtaining a methanol solution containing DFAL-hemiacetal. The thus-obtained solution was subjected to precision distillation (theoretical plate number: 35, distillation temperature: 92° C., vacuum degree: ~35 kPa) so as to separate therefrom a major portion of methanol. The distillation was continued after 850 g (19 mol) of ethanol was added to the distillation bottom. As a result, 450 g of difluoroacetaldehyde ethyl hemiacetal (DFAL-EtOH) was yielded as a fraction.

It was confirmed that, in the fraction, there were contained methanol, ethanol, β,β-difluoroethanol, methyl hemiacetal (DFAL-MeOH), ethyl hemiacetal (DFAL-EtOH), β,β-difluoroethyl hemiacetal of the following formula (i) and ethyl hemiacetal dimer of the following formula (ii).

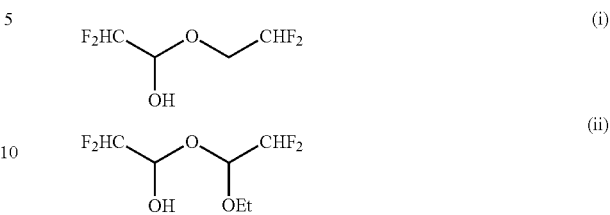

The purity (mol %) of the respective components were as follows: less than 0.1%; 5.6%; 3.3%; 1.8%; 87.3%; 0.6% and 1.5%. In view of the purity, the yield was about 30%.

[Analysis Method]

To more precisely examine composition changes of DFAL-EtOH over time, analysis quantitative analysis was performed by $^1$H-NMR and $^{19}$F-NMR according to the following method.

First, 0.15 mL of a sample and 50 mL of para(trifluoromethyl)(trifluoromethyl)benzene (PTF-TFM) as internal standard substance were respectively precisely weighed out. Next, 1.0 mL of deuterated chloroform was mixed with and dissolved in the sample and internal standard substance. Then, 0.55 mL of the solution was put into a NMR tube. The $^1$H and $^{19}$F spectra of the solution was measured by a NMR spectrometer (JNM-ECA400 manufactured by JEOL Ltd.) The chemical shifts of the respective components were as indicated below.

PTF-TFM: 7.53 to 7.93 ppm (4H)
DFAL-EtOH: 4.50 to 4.71 ppm (1H)
DFAL-MeOH: 3.51 to 3.53 ppm (3H)
DFAL-DFOL [$CF_2HCH(OH)OCH_2CF_2H$]: −125 to 126 ppm (2F)
Dimer: 4.92 to 5.11 ppm (1H)
Ethanol: 3.65 to 3.73 ppm (2H)
Methanol: 3.41 to 3.45 ppm (3H)
Free DFOL: −128 to −127 ppm (2F)
(The $^1$H spectrum measurement target was a H atom at 1-position in each of DFAL-EtOH, DFAL-MeOH and DFAL-DFOL. In the measurement, free methanol and free acetal were not detected.)

In each of the following examples, the sample was prepared in the same manner as in Synthesis Example 2. However, the initial amount of dimer in the sample was slightly larger in the following examples than in Synthesis Example 2 due to minor differences in the timing and the like of the post treatment. The dimer, once formed, was normally not converted back to the original hemiacetal or not converted to another chemical species. For this reason, the amount of dimer present at the initial stage (i.e. initiation of storage) was not regarded as a problem. Attention was focused on the amount of decrease of DFAL-hemiacetal and the amount of newly formed dimer during a storage period (one year).

In the following respective examples and comparative examples, the pH of the "2,2-difluoroacetaldehyde-alcohol composite system" at the initiation of storage was 8 as determined by dipping a pH paper; and the water content of the "2,2-difluoroacetaldehyde-alcohol composite system" at the initiation of storage was 180 to 200 ppm as determined by a Karl Fischer moisture meter.

[Example 1] Preservation Stability Test of DFAL-Hemiacetal

This example refers to the case where the ratio of the total alcohol amount to the total aldehyde amount (mole ratio) was 1.50. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 62.1 mol % of 1-ethoxy-2,2-difluoroethanol (DFAL-EtOH), 1.4 mol % of 2,2-difluoro-1-methoxyethanol, 1.4 mol % of difluoroethanol, 0.5 mol % of β,β-difluoroethyl hemiacetal (DFAL-DFOL), 4.0 mol % of dimer and 30.6 mol % of ethyl alcohol. This solution was stored at room temperature. After one year of storage, the solution had a composition of 60.8 mol % of 1-ethoxy-2,2-difluoroethanol (DFAL-EtOH), 1.3 mol % of 2,2-difluoro-1-methoxyethanol, 1.4 mol % of difluoroethanol, 0.4 mol % of DFAL-DFOL, 4.3 mol % of dimer and 31.8 mol % of ethyl alcohol. The composition changes of the solution over time are indicated in the following table.

TABLE 1

| DFAL-EtOH | Mol % | | | | | |
| --- | --- | --- | --- | --- | --- | --- |
| Storage period (months) | DFAL-EtOH | DFAL-MeOH | DFAL-DFOL | DFOL | EtOH | Dimer |
| 0 | 62.1 | 1.4 | 0.5 | 1.4 | 30.6 | 4.0 |
| 1 | 62.2 | 1.3 | 0.6 | 1.4 | 30.5 | 3.9 |
| 2 | 62.0 | 1.4 | 0.5 | 1.5 | 30.7 | 3.9 |
| 3 | 61.7 | 1.3 | 0.5 | 1.4 | 31.0 | 4.1 |
| 6 | 61.3 | 1.4 | 0.5 | 1.4 | 31.3 | 4.1 |
| 12 | 60.8 | 1.3 | 0.4 | 1.4 | 31.8 | 4.3 |

In Example 1 where the excess alcohol was present in an amount of 50 mol % based on the aldehyde, there was only a slight increase in the amount of the dimer even after one year of storage. Further, there was almost no change in the amount of the hemiacetal such as DFAL-EtOH, DFAL-MeOH and DFAL-DFOL even after one year of storage. It has thus been shown by these results that it was possible in Example 1 to significantly improve the preservation stability of the target compound as compared to the after-mentioned comparative examples.

[Example 2] Preservation Stability Test of DFAL-Hemiacetal

This example refers to the case where the ratio of the total alcohol amount to the total aldehyde amount was 1.23. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 75.8 mol % of 1-ethoxy-2,2-difluoroethanol (DFAL-EtOH), 1.5 mol % of 2,2-difluoro-1-methoxyethanol, 1.4 mol % of difluoroethanol, 0.6 mol % of β,β-difluoroethyl hemiacetal (DFAL-DFOL), 4.0 mol % of dimer and 16.7 mol % of ethyl alcohol. This solution was stored at room temperature. After one year of storage, the solution had a composition of 71.9 mol % of 1-ethoxy-2,2-difluoroethanol (DFAL-EtOH), 1.3 mol % of 2,2-difluoro-1-methoxyethanol, 1.3 mol % of difluoroethanol, 0.4 mol % of DFAL-DFOL, 4.8 mol % of dimer and 19.7 mol % of ethyl alcohol. The composition changes of the solution over time are indicated in the following table.

TABLE 2

| DFAL-EtOH | Mol % | | | | | |
| --- | --- | --- | --- | --- | --- | --- |
| Storage period (months) | DFAL-EtOH | DFAL-MeOH | DFAL-DFOL | DFOL | EtOH | Dimer |
| 0 | 75.8 | 1.5 | 0.6 | 1.4 | 16.7 | 4.0 |
| 1 | 75.2 | 1.5 | 0.6 | 1.4 | 17.2 | 4.0 |
| 2 | 75.0 | 1.4 | 0.5 | 1.5 | 17.5 | 4.1 |
| 3 | 74.5 | 1.3 | 0.6 | 1.4 | 17.3 | 4.5 |
| 6 | 73.8 | 1.4 | 0.5 | 1.3 | 18.3 | 4.6 |
| 12 | 71.9 | 1.3 | 0.4 | 1.3 | 19.7 | 4.8 |

It has been shown by these results that, in Example 2 where the excess alcohol was present in an amount of 23 mol % based on the aldehyde, the preservation stability of the target compound was good next to that in Example 1.

[Example 3] Preservation Stability Test of DFAL-Hemiacetal

This example refers to the case where the ratio of the total alcohol amount to the total aldehyde amount was 1.19. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 78.1 mol % of 1-ethoxy-2,2-difluoroethanol (DFAL-EtOH), 1.6 mol % of 2,2-difluoro-1-methoxyethanol, 1.4 mol % of difluoroethanol, 0.6 mol % of β,β-difluoroethyl hemiacetal (DFAL-DFOL), 4.1 mol % of dimer and 14.2 mol % of ethyl alcohol. This solution was stored at room temperature. After one year of storage, the solution had a composition of 74.4 mol % of 1-ethoxy-2,2-difluoroethanol (DFAL-EtOH), 1.3 mol % of 2,2-difluoro-1-methoxyethanol, 1.3 mol % of difluoroethanol, 0.4 mol % of DFAL-DFOL, 5.4 mol % of dimer and 17.1 mol % of ethyl alcohol. The composition changes of the solution over time are indicated in the following table.

TABLE 3

| DFAL-EtOH | Mol % | | | | | |
| --- | --- | --- | --- | --- | --- | --- |
| Storage period (months) | DFAL-EtOH | DFAL-MeOH | DFAL-DFOL | DFOL | EtOH | Dimer |
| 0 | 78.1 | 1.6 | 0.6 | 1.4 | 14.2 | 4.1 |
| 1 | 77.3 | 1.6 | 0.7 | 1.4 | 14.9 | 4.3 |
| 2 | 76.6 | 1.5 | 0.6 | 1.4 | 15.4 | 4.5 |
| 3 | 76.2 | 1.3 | 0.5 | 1.4 | 15.7 | 4.9 |
| 6 | 75.3 | 1.3 | 0.5 | 1.4 | 16.3 | 5.1 |
| 12 | 74.4 | 1.3 | 0.4 | 1.3 | 17.1 | 5.4 |

It has been shown by these results that, in Example 3 where the excess alcohol was present in an amount of 19 mol % based on the aldehyde, the preservation stability of the target compound was good next to those in Examples 1 and 2.

[Example 4] Preservation Stability Test of DFAL-Hemiacetal

This example refers to the case where the ratio of the total alcohol amount to the total aldehyde amount was 1.17. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 79.5 mol % of 1-ethoxy-2,2-difluoroethanol (DFAL-EtOH), 1.9 mol % of 2,2-difluoro-1-methoxyethanol, 0.9 mol % of difluoroethanol, 1.1 mol % of β,β-difluoroethyl hemiacetal (DFAL-DFOL), 3.7 mol % of dimer and 13.0 mol % of ethyl alcohol. This solution was stored at room temperature. After one year of storage, the solution had a composition of 74.6 mol % of 1-ethoxy-2,2-difluoroethanol (DFAL-EtOH), 1.6 mol % of 2,2-difluoro-1-methoxyethanol, 1.1 mol % of difluoroethanol, 0.8 mol % of DFAL-DFOL, 5.8 mol % of dimer and 16.1 mol % of ethyl alcohol. The composition changes of the solution over time are indicated in the following table.

TABLE 4

| DFAL-EtOH | Mol % | | | | |
|---|---|---|---|---|---|
| Storage period (months) | DFAL-EtOH | DFAL-MeOH | DFAL-DFOL | DFOL | EtOH | Dimer |
| 0 | 79.5 | 1.9 | 1.1 | 0.9 | 13.0 | 3.7 |
| 1 | 78.1 | 1.8 | 1.1 | 1.0 | 13.6 | 4.1 |
| 2 | 77.6 | 1.9 | 0.9 | 0.9 | 14.1 | 4.6 |
| 3 | 77.1 | 1.7 | 0.8 | 0.9 | 14.4 | 4.9 |
| 6 | 76.0 | 1.7 | 0.7 | 1.0 | 15.8 | 5.1 |
| 12 | 74.6 | 1.6 | 0.8 | 1.1 | 16.1 | 5.8 |

It has been shown by these results that, even in Example 4 where the excess alcohol was present in an amount of 17 mol % based on the aldehyde, the preservation stability of the target compound was good with almost no composition changes over one year.

[Comparative Example 1] Preservation Stability Test of DFAL-Hemiacetal

This comparative example refers to the case where the ratio of the total alcohol amount to the total aldehyde amount was 1.11. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 83.5 mol % of 1-ethoxy-2,2-difluoroethanol (DFAL-EtOH), 1.6 mol % of 2,2-difluoro-1-methoxyethanol, 0.6 mol % of difluoroethanol, 1.0 mol % of β,β-difluoroethyl hemiacetal (DFAL-DFOL), 4.3 mol % of dimer and 9.0 mol % of ethyl alcohol. This solution was stored at room temperature. After one year of storage, the solution had a composition of 74.7 mol % of 1-ethoxy-2,2-difluoroethanol (DFAL-EtOH), 1.4 mol % of 2,2-difluoro-1-methoxyethanol, 0.8 mol % of difluoroethanol, 0.7 mol % of DFAL-DFOL, 9.7 mol % of dimer and 12.8 mol % of ethyl alcohol. The composition changes of the solution over time are indicated in the following table.

TABLE 5

| DFAL-EtOH | Mol % | | | | |
|---|---|---|---|---|---|
| Storage period (months) | DFAL-EtOH | DFAL-MeOH | DFAL-DFOL | DFOL | EtOH | Dimer |
| 0 | 83.5 | 1.6 | 1.0 | 0.6 | 9.0 | 4.3 |
| 1 | 80.4 | 1.4 | 0.8 | 0.5 | 10.8 | 6.1 |
| 2 | 78.6 | 1.5 | 0.7 | 0.6 | 11.3 | 7.1 |
| 3 | 78.0 | 1.3 | 0.8 | 0.7 | 11.9 | 7.3 |
| 6 | 76.0 | 1.4 | 0.6 | 0.8 | 13.1 | 8.1 |
| 12 | 74.7 | 1.4 | 0.7 | 0.8 | 12.8 | 9.7 |

In Comparative Example where the excess alcohol was present in an amount of 11 mol % based on the aldehyde, the amount of increase of the dimer during the lapse of one year was 5% or more as indicated above. Further, there was seen an apparent increase in the amount of the free ethanol. The reason for this is assumed that two molecules of DFAL-EtOH were reacted to form the dimer and release one remaining molecule of ethanol.

[Comparative Example 2] Preservation Stability Test of DFAL-Hemiacetal

This comparative example refers to the case where the ratio of the total alcohol amount to the total aldehyde amount was 1.07. The total alcohol amount was determined as the total mole number of 1-ethoxy-2,2-difluoroethanol (DFAL-EtOH), 2,2-difluoro-1-methoxyethanol, β,β-difluoroethyl hemiacetal (DFAL-DFOL), difluoroethanol and ethyl alcohol. The total aldehyde amount was determined as the total mole number of 1-ethoxy-2,2-difluoroethanol (DFAL-EtOH), 2,2-difluoro-1-methoxyethanol and β,β-difluoroethyl hemiacetal (DFAL-DFOL).

The sample prepared was a solution containing 86.7 mol % of 1-ethoxy-2,2-difluoroethanol (DFAL-EtOH), 0.9 mol % of 2,2-difluoro-1-methoxyethanol, 1.5 mol % of difluoroethanol, 0.7 mol % of β,β-difluoroethyl hemiacetal (DFAL-DFOL), 4.7 mol % of dimer and 5.7 mol % of ethyl alcohol. This solution was stored at room temperature. After one year of storage, the solution had a composition of 71.2 mol % of 1-ethoxy-2,2-difluoroethanol (DFAL-EtOH), 0.7 mol % of 2,2-difluoro-1-methoxyethanol, 1.3 mol % of difluoroethanol, 0.8 mol % of difluoroethyl hemiacetal (DFAL-DFOL), 12.5 mol % of dimer and 13.4 mol % of ethyl alcohol. The composition changes of the solution over time are indicated in the following table.

TABLE 6

| DFAL-EtOH | Mol % | | | | |
|---|---|---|---|---|---|
| Storage period (months) | DFAL-EtOH | DFAL-MeOH | DFAL-DFOL | DFOL | EtOH | Dimer |
| 0 | 86.7 | 0.9 | 0.7 | 1.5 | 5.7 | 4.7 |
| 1 | 82.3 | 0.9 | 0.6 | 1.5 | 7.8 | 6.9 |

TABLE 6-continued

| DFAL-EtOH | | | Mol % | | | |
|---|---|---|---|---|---|---|
| Storage period (months) | DFAL-EtOH | DFAL-MeOH | DFAL-DFOL | DFOL | EtOH | Dimer |
| 2 | 79.5 | 0.9 | 0.6 | 1.5 | 9.1 | 8.4 |
| 3 | 77.7 | 0.8 | 0.7 | 1.4 | 10.1 | 9.3 |
| 6 | 74.4 | 0.8 | 0.8 | 1.4 | 11.9 | 10.7 |
| 12 | 71.2 | 0.7 | 0.8 | 1.3 | 13.4 | 12.5 |

Even in Comparative Example 2 where the excess alcohol was present in an amount of 7 mol % based on the aldehyde, there were seen significant increases in the amount of the dimer and the amount of the free ethanol after the lapse of one year. Such a composition is not always suitable for storage over several months to one year (even though the stability of the composition can be ensured for a short term. The significant effects of the presence of 15% or more of the excess alcohol in the composite system of the present invention have been verified by the above results.

INDUSTRIAL APPLICABILITY

The stabilization method of 2,2-difluoroacetaldehyde according to the present invention is expected to be useful for preservation and distribution as an intermediate for production of pharmaceutical and agrichemical products.

The invention claimed is:

1. A method for improving preservation stability of 2,2-difluoroacetaldehyde, comprising:
a first step of forming a 2,2-difluoroacetaldehyde-alcohol composite system that contains a hemiacetal of the 2,2-difluoroacetaldehyde as represented by the formula (3) and a free alcohol as represented by the formula (2)

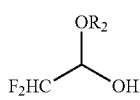  (3)

where $R^2$ represents a $C_1$-$C_6$ linear, branched or cyclic hydrocarbon group in which a part or all of hydrogen atoms may be substituted with a fluorine atom

where $R^2$ has the same definition as in the formula (3); and
a second step of storing the 2,2-difluoroacetaldehyde-alcohol composite system in a storage container,
wherein, at the initiation of storage of the 2,2-difluoroacetaldehyde-alcohol composite system in the storage container, the 2,2-difluoroacetaldehyde-alcohol composite system has a substantially neutral pH and a water content of 1000 ppm or lower; and
wherein, at the initiation of storage of the 2,2-difluoroacetaldehyde-alcohol composite system in the storage container, the total molar amount of the alcohol in the 2,2-difluoroacetaldehyde-alcohol composite system is 1.15 to 4.00 times the total molar amount of the 2,2-difluoroacetaldehyde.

2. The method for improving preservation stability of 2,2-difluoroacetaldehyde according to claim 1, wherein the total molar amount of the alcohol is 1.15 to 1.60 times the total molar amount of the 2,2-difluoroacetaldehyde.

3. The method for improving preservation stability of 2,2-difluoroacetaldehyde according to claim 2, wherein the alcohol represented by the formula (2) is an alcohol having 1 to 6 carbon atoms.

4. The method for improving preservation stability of 2,2-difluoroacetaldehyde according to claim 3, wherein the alcohol represented by the formula (2) is at least one of methanol and ethanol.

5. The method for improving preservation stability of 2,2-difluoroacetaldehyde according to claim 2, wherein the second step is performed at a storage temperature of −30 to +50° C.

6. The method for improving preservation stability of 2,2-difluoroacetaldehyde according to claim 5, wherein the second step is performed at a storage temperature of +10 to +45° C.

7. The method for improving preservation stability of 2,2-difluoroacetaldehyde according to claim 6, wherein the second step is performed at a storage temperature of +20 to +35° C.

8. The method for improving preservation stability of 2,2-difluoroacetaldehyde according to claim 3, wherein the second step is performed at a storage temperature of −30 to +50° C.

9. The method for improving preservation stability of 2,2-difluoroacetaldehyde according to claim 8, wherein the second step is performed at a storage temperature of +10 to +45° C.

10. The method for improving preservation stability of 2,2-difluoroacetaldehyde according to claim 9, wherein the second step is performed at a storage temperature of +20 to +35° C.

11. The method for improving preservation stability of 2,2-difluoroacetaldehyde according to claim 1, wherein the alcohol represented by the formula (2) is an alcohol having 1 to 6 carbon atoms.

12. The method for improving preservation stability of 2,2-difluoroacetaldehyde according to claim 11, wherein the alcohol represented by the formula (2) is at least one of methanol and ethanol.

13. The method for improving preservation stability of 2,2-difluoroacetaldehyde according to claim 11, wherein the second step is performed at a storage temperature of −30 to +50° C.

14. The method for improving preservation stability of 2,2-difluoroacetaldehyde according to claim 13, wherein the second step is performed at a storage temperature of +10 to +45° C.

15. The method for improving preservation stability of 2,2-difluoroacetaldehyde according to claim 14, wherein the second step is performed at a storage temperature of +20 to +35° C.

16. The method for improving preservation stability of 2,2-difluoroacetaldehyde according to claim 1, wherein the second step is performed at a storage temperature of −30 to +50° C.

17. The method for improving preservation stability of 2,2-difluoroacetaldehyde according to claim 16, wherein the second step is performed at a storage temperature of +10 to +45° C.

18. The method for improving preservation stability of 2,2-difluoroacetaldehyde according to claim 17, wherein the second step is performed at a storage temperature of +20 to +35° C.

* * * * *